US012758293B2

(12) United States Patent
Brugada Terradellas et al.

(10) Patent No.: US 12,758,293 B2
(45) Date of Patent: Oct. 13, 2026

(54) CRYOGENIC BIPARIETAL ABLATION CATHETER AND ABLATION SYSTEM COMPRISING SUCH AN ABLATION CATHETER

(71) Applicant: Marijke Irene Van Der Laan, Verbier (CH)

(72) Inventors: Pedro Brugada Terradellas, Verbier (CH); Kornelis Jan Willem Cordia, Verbier (CH)

(73) Assignee: Marijke Van Der Laan, Verbier (CH)

( * ) Notice: Subject to any disclaimer, the term of this patent is extended or adjusted under 35 U.S.C. 154(b) by 188 days.

(21) Appl. No.: 18/406,629

(22) Filed: Jan. 8, 2024

(65) Prior Publication Data

US 2024/0225711 A1 Jul. 11, 2024

(30) Foreign Application Priority Data

Jan. 9, 2023 (NL) ..................................... 2033927

(51) Int. Cl.
*A61B 18/02* (2006.01)
*A61B 18/00* (2006.01)
*A61M 25/10* (2013.01)

(52) U.S. Cl.
CPC .... *A61B 18/02* (2013.01); *A61B 2018/00357* (2013.01); *A61B 2018/00363* (2013.01);
(Continued)

(58) Field of Classification Search
CPC .......... A61B 18/02; A61B 2018/00363; A61B 2018/00577; A61B 2018/00744;
(Continued)

(56) References Cited

U.S. PATENT DOCUMENTS

2006/0069385 A1* 3/2006 Lafontaine ............. A61B 18/02 606/23
2021/0338265 A1* 11/2021 Cohn ..................... A61B 34/10

FOREIGN PATENT DOCUMENTS

EP 3682830 A1 7/2020
EP 3943032 A1 * 1/2022 ........... A61B 8/1492
(Continued)

*Primary Examiner* — Joanne M Rodden
*Assistant Examiner* — Abigail Bock
(74) *Attorney, Agent, or Firm* — Myers Bigel, P.A.

(57) ABSTRACT

In an aspect of the present disclosure, an ablation catheter system is provided for biparietal tissue ablation, said catheter comprising: a flexible epicardial catheter unit comprising a magnet and an ablation element, wherein said magnet is located at a wall section of said catheter unit for magnetic external driving and eventually coupling of said magnet with a magnet of said endocardial catheter unit, and wherein said ablation element is configured as an elongated ablation element along a longitudinal direction of said flexible epicardial catheter unit; a flexible endocardial catheter unit comprising a magnet and an ablation element, wherein said magnet is located at a wall section of said catheter unit for magnetic external driving and eventually coupling of said magnet with said magnet of said epicardial catheter unit, and wherein said ablation element is configured as an elongated ablation element along a longitudinal direction of said flexible endocardial catheter unit; said elongated ablation element of both said epicardial and said endocardial catheter unit comprising:

an ablation balloon, and a protective balloon, wherein said ablation balloon is arranged for cryoablation of said operative tissue with a freezing medium flowing through a first exhaust port in a wall section of said catheter into said ablation balloon for subjecting said operative tissue with cold of said freezing medium, and wherein said protective balloon is arranged for protect- (Continued)

ing tissue and/or anatomic structures surrounding said operative tissue with a thermal medium flowing through a second exhaust port in a wall section of said catheter into said protective balloon, and wherein said ablation balloon and said protective balloon are configured for, in use, said ablation balloon to be surrounded by said protective balloon, for protecting said surrounding tissue and/or anatomic structures by removing thermal energy of said freezing medium affecting said surrounding tissue and/or anatomic structures.

15 Claims, 5 Drawing Sheets

(52) U.S. Cl.
CPC ............... *A61B 2018/00577* (2013.01); *A61B 2018/00744* (2013.01); *A61B 2018/00839* (2013.01); *A61B 2018/0212* (2013.01); *A61B 2018/0262* (2013.01); *A61M 25/1011* (2013.01); *A61M 2025/1013* (2013.01); *A61M 25/1018* (2013.01); *A61M 25/10184* (2013.11); *A61M 2025/1093* (2013.01)

(58) Field of Classification Search
CPC .. A61B 2018/00839; A61B 2018/0212; A61B 2018/0262; A61M 25/10184; A61M 25/1018; A61M 25/1011; A61M 2025/1013; A61M 2025/1093
See application file for complete search history.

(56) References Cited

FOREIGN PATENT DOCUMENTS

| | | | | | |
|---|---|---|---|---|---|
| EP | 3998030 | A1 | | 5/2022 | |
| EP | 3998030 | B1 | * | 9/2025 | ............. A61B 18/02 |
| WO | 2013013098 | A1 | | 1/2013 | |
| WO | 2020104462 | A1 | | 5/2020 | |

* cited by examiner

CRYOGENIC BIPARIETAL ABLATION CATHETER AND ABLATION SYSTEM COMPRISING SUCH AN ABLATION CATHETER

CROSS-REFERENCE TO RELATED APPLICATIONS

This application claims priority to and the benefit of Netherlands Patent Application No. 2033927, filed Jan. 9, 2023, the disclosure of which is hereby incorporated by reference in its entirety.

FIELD OF THE INVENTION

The invention is in the field of treatment of atrial and ventricular arrhythmias through cryogenic ablation. In particular, it provides an ablation catheter arranged to perform true biparietal ablation.

BACKGROUND OF THE INVENTION

Despite the fact that there have been many advances in the treatment of Atrial Fibrillation, AF, over the past years, this cardiac arrhythmia is still a major cause of morbidity and mortality worldwide. It has been estimated that the number of patients with AF in 2030 in Europe will be 14-17 million and AF will be responsible for 3.5-4 million hospitalizations for AF, and 100-120 million outpatient visits.

Due to this major burden of AF, a number of approaches have been developed to treat this arrhythmia and different lesion sets have been introduced. Nonetheless, neither the catheter ablation, carried out by cardiologists who make endocardial lesions through a femoral approach, or surgical techniques (standard or minimally-invasive approach) have gained optimal results, in particular in long-standard persistent atrial fibrillation in which structural changes (remodelling) occur in addition to electrical disarrangement.

However, other arrhythmias may also be the target of this invention.

Premature ventricular contractions (PVCs) are relatively common and can be detected in 75% of healthy persons using 48-h Holter. Several studies have demonstrated that radiofrequency ablation was more efficient than pharmacological therapy for eliminating PVCs that can lead to cardiomyopathy. Nonetheless, while a significant reduction in PVC burden was observed consistently across patients with PVC with different localizations, clinical success was significantly lower in patients with PVC originating from the non-outflow tract left ventricular regions.

Ventricular tachycardia (VT) is an abnormal rapid heart rhythm originating from the lower pumping chambers of the heart (ventricles) and it may end to ventricular fibrillation (VF) which will cause sudden cardiac death. The success of VT ablation with the tools in our hands varies depending on the patient's specific heart condition that caused VT. The procedure is most effective in patients with otherwise normal hearts, where the success rate is above 90%. In patients with structural heart disease due to scar or cardiomyopathy, success rates range between 50-75% at 6-12 months.

Ventricular Fibrillation. Ventricular activation during VF is apparently disorganized, making mapping and interpretation difficult. Prolonged mapping during VF would require mechanical circulatory support as VF causes complete hemodynamic collapse. These limitations have been addressed by the realization that there is often a reliable trigger arrhythmia that initiates the clinical VF episodes, and an approach to map and ablate this trigger can be successful. Such triggers can be PVCs localizing to the Purkinje/fascicular system, and in other cases can be ectopy from outflow tracts or intracavitary structures like papillary muscles. More recently, approaches beyond trigger elimination directly targeting the VF substrate have been proposed but not well established yet. Catheter stability, which is not ensured by the catheter in use, is particularly relevant for the success of the procedure.

Brugada syndrome (BrS) is a heterogeneous disease due to a combination of various degrees of electrical, genetic, and structural abnormalities. It is a life threatening diseases that can lead to sudden death even in young asymptomatic and apparently normal subjects. Promising results have been described in ablating the arrhythmogenic substrate of the epicardial right ventricular outflow tract (LVOT). Approaching and treating the LVOT target from both surfaces would significantly improve results enhancing a more effective substrate modification.

The Wolff-Parkinson-White (WPW) syndrome is generally benign and therapy is usually provided for the relief of symptoms associated with arrhythmia, usually recurrent paroxysmal supraventricular tachycardia. A critical further consideration is the potential for the occurrence of atrial fibrillation or flutter which may result in sudden cardiac death. Catheter ablation has been proven as effective and safe therapy for patients with symptomatic Wolff-Parkinson-White (WPW) syndrome. Long term results of the ablation require an improvement of the technique.

Other arrhythmias that could benefit from the ablation catheter leading a more effective treatment are: Atrioventricular reentrant tachycardia (AVRT) associated with the Wolff-Parkinson-White (WPW) syndrome or a concealed accessory pathway, Atrioventricular nodal reentrant tachycardia (AVNRT), Atrial tachycardia, Atrial flutter, AV nodal ablation with pacemaker implantation, Frequent ventricular ectopy with refractory symptoms or associated cardiomyopathy.

It is now accepted worldwide that several reasons can be identified for such unsatisfactory results following ablation procedures of atria and ventricular arrhythmias.

Firstly, the inability of available catheters to make accurate and durable transmural lesions under different circumstances and arrhythmia substrates with the result of recurrent disease due to re-activation of foci within ablated areas which requires patient hospital re-admission and pharmacological new treatment and/or reoperation.

Secondly, with the tools currently available it is impossible to perform effective linear lesions to complete, for instance, the complete left posterior wall isolation in AFor continuous long transmural lesion to effectively target the foci of other atrial aor ventricula arrhythmias. This is not achievable with the available tools because very often patients came back with foci of arrhythmia localized in these area that demonstrates the lack of efficacy of these tools.

Thirdly, previous studies of the inventors have demonstrated that the ablations from both side of the heart walls are more effective than the same procedure only carried out from either epicardial and endocardial surface taken alone. The inefficacy of the current treatment may be due to such uniparietal treatments. Furthermore, despite many attempts have been made to approach the lesion area from both epicardial and endocardial walls, there is no tool on the market that can ensures a simultaneous biparietal ablation on the targeted area of the arrhythmia.

The cryogenic energy technique is based on the adsorption of energy when the gas used (Nitrous oxide or Argon)

switches from liquid to gas state, resulting in the rapid cooling of the tissue leading to cellular death. Cryo energy has been demonstrated to be superior to other energy sources with the great advantages with keeping the original architecture of the tissue. This characteristic makes the cryo ablation safer than the others, especially when the ablation has to be performed in areas close to vascular structures (coronary arteries).

Furthermore, the cryo energy helps to overcome important challenges for an effective biparietal ablation. Indeed, a perfect coupling between the endocardial and epicardial catheter is mandatory to get effective lesions and to obtain such a coupling supplemental energy (magnetism) are necessary. In contrast, Cryo energy allows a steady and durable ice-mediated adhesion to the walls that can be easily modified through the temperature setup. Furthermore such ice-mediated mechanism help obtain a complete stabilization of the catheter that is a drawback of the catheters in use for arrhythmias. Likely, the biparietal application of cryo energy may overcome one of the potential drawbacks of this technique. Indeed, the presence of the blood in the cardiac chambers, acting as heat sink, hampers the propagation of the cold energy to the targeted tissue. In contrast, with a biparietal application, the targeted tissue is fixed interposed between the cryo catheters, hit by the cold energy without the interposition of blood.

Finally, the biparietal application of the cryo energy avoids the risk of clots caused by the blood-cold surface-direct contact that represent an important shortcoming of uniparietal cryo application.

So far, no tool exists in the market capable of making biparietal lesion with the employment cryo energy.

Finally, two of the most feared and life-threatened complications during ablation procedures is represented by oesophageal lesions and recurrent vagal nerve injury. To date, the tools available on the market do not provide protection for these structures.

More recently ablation procedures have emerged that use a hybrid approach. This technique, carried out by a cardiothoracic surgeon and a cardiologist in synchrony, combines the epicardial surgical transthoracic approach with the endocardial trans femoral approach. Unfortunately, after a promising start, results are not fully satisfactory. One of the most likely reason may be that no specific tools have yet been designed for the hybrid approach. Secondly, as it is being performed now, the procedure is not truly hybrid since endocardial ablations are often performed after the epicardial and lesions are only made by the cardiologist whether and when residual electrical activity is detected. Likewise, current approaches require bilateral thoracoscopy. Bilateral thoracoscopy required opening both pleural spaces and keeping the ipsilateral lung deflated, both significantly influencing morbidity and patient's recovery since the tools employed do not allow fast procedures.

A subxiphoid access may ensure a direct access to the atrial walls as well as the ventricular walls without opening the pleural spaces with great advantage of a shorter patient's postoperative recovery and lower complication rate.

As a result of all the above drawbacks described, arrhythmias can only very rarely, if ever, be treated by one single surgical ablation procedure. Almost always subsequent surgical ablation procedures have to be performed on the patient. Not only is this a major drawback for patients themselves, but it also represents a significant economic burden with overuse of healthcare resources, e.g. surgeons, operating rooms, etc.

As such, there is a pressing need for improved treatments by catheter ablation more effective then currently known ablation procedures.

SUMMARY OF THE INVENTION

It is an object of the present invention to provide an improved ablation catheter for tissue ablation such as premature ventricular contractions, Ventricular tachycardia, Ventricular Fibrillation. Brugada syndrome, Wolff-Parkinson-White syndrome, Atrioventricular reentrant tachycardia, Atrioventricular nodal reentrant tachycardia, Atrial tachycardia, Atrial flutter, AV nodal ablation with pacemaker implantation and Frequent ventricular ectopy with refractory symptoms or associated cardiomyopathy which ablation catheter solves at least some of the above-mentioned drawbacks of currently known ablation catheters.

It is a further object of the present invention to provide an improved true hybrid (in-one-step) bipolar ablation catheter employing cryo energy, which is able to create transmural lesions.

This is accomplished in a first aspect of the invention by an cryo ablation catheter for tissue ablation. The tissue is in particular heart tissue and the ablation any one or more of atrial, ventricular and atrio-ventricular arrhythmias.

In a first aspect there is provided, an ablation catheter system for tissue ablation such as atrial fibrillation, arranged for creating a transmural lesion of operative tissue of a subject, said catheter comprising:

- a flexible epicardial catheter unit comprising a magnet and an ablation element, wherein said magnet is located at a wall section of said catheter unit for magnetic coupling of said magnet with a magnet of said endocardial catheter unit, and wherein said ablation element is configured as an elongated ablation element along a longitudinal direction of said flexible epicardial catheter unit;
- a flexible endocardial catheter unit comprising a magnet and an ablation element, wherein said magnet is located at a wall section of said catheter unit for magnetic coupling of said magnet with said magnet of said epicardial catheter unit, and wherein said ablation element is configured as an elongated ablation element along a longitudinal direction of said flexible endocardial catheter unit;
- said elongated ablation element of both said epicardial and said endocardial catheter unit comprising:
- an ablation balloon, and
- a protective balloon,
- wherein said ablation balloon is arranged for cryoablation of said operative tissue with a freezing medium flowing through a first exhaust port in a wall section of said catheter into said ablation balloon for subjecting said operative tissue with cold of said freezing medium, and
- wherein said protective balloon is arranged for protecting tissue and/or anatomic structures surrounding said operative tissue with a thermal medium flowing through a second exhaust port in a wall section of said catheter into said protective balloon, and
- wherein said ablation balloon and said protective balloon are configured for, in use, said ablation balloon to be surrounded by said protective balloon, for protecting said surrounding tissue and/or anatomic structures by removing thermal energy of said freezing medium affecting said surrounding tissue and/or anatomic structures.

The present ablation catheter system comprises several components, at least comprising a first and second catheter unit, one being the epicardial catheter, the other the endocardial catheter. Both catheters comprise a magnet and an ablation element. The magnet is provided to guide and put in place—the two catheters as freeze attracts and keep in place such that the catheters. To this end, the magnet, or in an another example, a set of magnets, are located in a wall section of the unit, hence in the longitudinal direction thereof and preferably at or near the tip of the catheter.

The catheters thus also comprise an ablation element. The ablation element is comprised of two main components, one being the actual ablation element, which destroys the tissue, in the context of this description also referred to as the operative tissue of the subject, e.g., the human which is operated. The ablation element is a cryoablation element, which ablates the tissue by (extreme) cold. The temperature may depend on the type of cooling medium used for the cryo process, which might be a nitrogen oxide-based medium, carbon dioxide or carbon monoxide based medium, and on the length of the procedure. The medium may provide cold (sub-zero) sufficient to freeze the tissue and thereby ablate the tissue. More in particular the temperature may be as low as −10 degrees, or even −50 degree, more preferably −70 degrees or lower.

In recent years several different medical procedures are used to perform ablation, a techniques typically used is radio frequency based ablation, however, cryo ablation has more recently been determined to be preferable in many applications. A challenge of cryo ablation is however the control of the thermal energy. Preferably, the cold to which the operative tissue is subjected should be controlled in a precise manner in respect of temperature, duration and especially the location of the tissue. When the operative tissue has been targeted, it is required that the surrounding tissue and the anatomic structures near or adjacent to the operative tissue is affected as little as possible by the cold of the freezing medium upon performing the cryo ablation procedure.

Hence, on the one hand accurate control of temperature properties is required, and on the other hand accurate control of the targeted area to avoid adversely affecting the non-targeted areas and tissue and anatomic structures located there. Of these two challenges, the temperature may be controlled in an accurate manner by volume, and flow rate of the freezing medium. More of a challenge lies in the accurate control of the target area and preventing non-targeted area from the cold of the freezing medium.

To this extend, the ablation system of the present disclosure, and in particular the elongated ablation element of both the epicardial and the endocardial catheter unit comprises both an ablation balloon and a protective balloon, wherein the ablation balloon on the one hand, is arranged for cryoablation of the operative tissue with a freezing medium flowing through a first exhaust port in a wall section of the catheter into the ablation balloon for subjecting the operative tissue with cold of the freezing medium. The protective balloon on the other hand is arranged for protecting tissue and/or anatomic structures surrounding the operative tissue with a thermal medium flowing through a second exhaust port in a wall section of the catheter into the protective balloon.

To assure a high contrast between targeted and non-target areas, i.e. the operative tissue and the tissue and/or anatomic structures surrounding the operative tissue, the ablation balloon and the protective balloon are configured such that, when in use and thus, when the balloons are inflated, the ablation balloon to be surrounded by the protective balloon, for protecting the surrounding tissue and/or anatomic structures by removing thermal energy of the freezing medium affecting the surrounding tissue and/or anatomic structures.

Cryogenic energy sources in itself are already used for cryo balloon circumferential pulmonary veins ablation from the inner left atrium approach. From the epicardial side, it is used through linear tools. The most beneficial features of cryogenic energy reside in preserving of integrity of collagen tissue, thus preserving tissue architecture. This characteristic is beneficial where ablation of the perivascular tissue is needed. The most important drawback is a longer length of the procedure and scarce results in terms of transmurality when employed on a beating heart limited by heat from intracardiac blood flow and when it is employed on a side of the heart. Another frequent issue of cryogenic energy is represented by the not full control of the spread of the lesion. Indeed, cryoablation can still pose a significant threat to collateral structures such as the esophagus, lungs, coronary arteries, and phrenic and vagus nerves. More specifically ulcerative esophageal lesions, bronchial injury, phrenic nerve injury (PNI) and cryo injury of endocardial structures. Another important issue is the impact of blood flow on lesion size. That is, increased blood flow surrounding the ablation catheter can significantly attenuate the size of cryolesions. A major barrier to clinical adoption of hybrid simultaneous ablation however, is the lack of tools, specifically catheters and sheaths, designed for use specifically for hybrid procedures.

To overcome the limitations of known catheters, the system of the present disclosure provides, but is not limited thereto, a means for achieving a true hybrid ablation employing two cryo balloons at the same time, introduced into the chest via a subxiphoid point of entry (alternatively through a right or left thoracoscopic port, a left or right thoracothomy or, through a sternotomy). The endocardial catheter is placed through the femoral vessels but, alternatively also through the neck or the arm vessels and transseptal puncture.

The two cryo balloons will be enclosed and surrounded by a protective balloon to protect the structures surrounding the lesions targets from freezing damage.

It is expressed, that the system can be employed for ablation of atrial fibrillation, Premature ventricular contractions, Ventricular tachycardia, Ventricular Fibrillation. Brugada syndrome, Wolff-Parkinson-White syndrome, Atrioventricular reentrant tachycardia, Atrioventricular nodal reentrant tachycardia, Atrial tachycardia, Atrial flutter, AV nodal ablation with pacemaker implantation and Frequent ventricular ectopy with refractory symptoms or associated cardiomyopathy. The catheter is however highly suitable for atrial fibrillation and ventricular arrhythmias.

The ablation catheter system according to the present disclosure allows epicardial access through the subxiphoid area of the chest. In an example, the a designated introduction kit may be employed including a needle, a sheath, a stiff guidewire, a dilator, to advance the probe into the posterior thoracic cavity.

Specific introduction kits will be designed for alternative approaches (right or left thoracoscopy, left or right thoracotomy or sternotomy). The endocardial catheter is placed, using specifically designed introduction tools, through the femoral vessels or, alternatively through the neck or the arm vessels.

One flexible epicardial catheter to be placed through a subxiphoid access into the chest reaching the heart's surface posterior wall. One endocardial catheter to be put through a big vessel of the les, neck or arms. In AF ablation after reaching the right atrium and crossing the atrial septum trough a septal puncture, the catheter reaches the final location into the left atrium.

The epicardial catheter is a cryo-ablation catheter system for ablation of epicardial tissue of a heart of a subject. The system comprising: an ablation catheter with a distal end, proximal end, and longitudinal body with several suction apertures.

To arrive at its desired position, the epicardial catheter unit should be flexible to be able to bended down and posteriorly to the heart to reach the target structures. To this end, the catheter according to the present disclosure is flexible and more in particular bendable and even more in particular bendable in a steerable manner.

When carrying out a subxiphoid access, the epicardial catheter unit should preferably be arranged to make are three separate turns: (1) A 90 degree turn immediately after entering the pericardial space, (2) a 130 degree (approximate and variable) at the apex of the heart, and (3) a final positioning turn (variable) right at the ablation side. The epicardial catheter unit is arranged to by comprising steering means.

In an example, at least one or both of the epicardial and the endocardial catheter unit further comprises a steerable catheter body.

In a further example, the steerable catheter body comprises longitudinal tension elements.

In an yet another further example, the longitudinal tension elements comprise a plurality of parallel steel tendons, disposed longitudinal in a wall section of said catheter body.

Preferably, the catheter comprises four steel tendons embedded in the outer diameter of the body of the probe. By simultaneous pull and push application to a couple of opposite wires the bending of the catheter is achieved. This is obtained by a corkscrew motion or rotation of the control or more particular steering system of the unit that allows easy guidance by the operator.

The freezing medium from the intake point reaches the freezing balloon or also referred to as the ablation balloon. The cooling entering the intake point ensures the insufflation of the cooling balloon that surrounds the ablation balloon, and that, through small holes in its inferior surface, enhances the irrigation of the pericardial space with temperature-controlled fluid. The suction od such a cooling fluid will be carried out by the aspiration from small holes at the tip of the catheter. The epicardial catheter does not show holes in the cooling balloon that is inflated using a closed-circuit to avoid patient's fluid overload. Therefore, a suction system it is not necessary. This close circuit design can be applied also to the epicardial.

In an example, at least one or both of the epicardial and the endocardial catheter units comprise parallel longitudinal channels, connecting the first and second exhaust ports for transport of the freezing medium and the thermal medium, respectively.

In an example, at least one or both of the epicardial and the endocardial catheter units comprise at least one parallel longitudinal channel connecting the first exhaust ports for transport of the freezing medium to the ablation balloon, and at least one parallel longitudinal channel connecting the second exhaust ports for transport of the thermal medium to the protective balloon, respectively, and at least one parallel longitudinal channel connecting an exhaust ports for removing the freezing medium and the thermal medium away from the ablation balloon and the thermal balloon.

In an example, at least one or both of the epicardial and the endocardial catheter units comprise one or more electrodes for a pre and post-operative evaluation of electrical potential of the targeted areas.

In an example, the freezing medium comprises one or more of the group of: nitrogen oxide, carbon dioxide, cooling liquid, cooling gas and Argon (Ar).

In an example, the system further comprises a subxiphoid introduction trocar.

In an example, the magnet of at least one or both of the epicardial and the endocardial catheter units comprise a magnet in a wall section corresponding to a section housing the ablation balloon, directing towards the operative tissue, for epicardial catheter unit and the endocardial catheter unit to be driven from the external side by applying different magnetic fields, and checking the correct alignment through a real-time video monitoring In an example, the protective balloon of at least one or both of the epicardial and the endocardial catheter units having larger dimensions than the ablation balloon.

In an example, the first exhaust port of at least one or both of the epicardial and the endocardial catheter units comprise a pattern of first exhaust subports, disposed in a one or preferably two-dimensional array of subports.

In an example, the second exhaust port of at least one or both of the epicardial and the endocardial catheter units comprise a pattern of first exhaust subports, disposed in a one or preferably two-dimensional array of subports.

In an example, the subports are disposed in a two-dimensional array, disposed at regular intervals along a longitudinal direction of the catheter.

In a further aspect, there is provided, an ablation catheter system for tissue ablation such as atrial fibrillation, arranged for creating a transmural lesion of operative tissue of a subject, the catheter comprising:

- an epicardial catheter unit according to any of the previous claims 1-14;
- an endocardial catheter unit according to any of the previous claims 1-14
- a medium supply arrangement, arranged for providing freezing medium and thermal medium to an ablation element, a group of ablation elements, or all ablation elements, of the epicardial and endocardial catheter unit either consecutively or simultaneously;
- a control unit arranged for controlling steering of at least one or both of the epicardial and the endocardial catheter units and for controlling inflating, deflating and flow of freezing medium and thermal medium to the epicardial and endocardial catheter unit.

In addition, as described above, a pre-formed shaft could be introduced through the suction lumen to place the catheter and removed once in place before starting the cryoablation procedure.

The epicardial probe will be approximately 30 cm and the cryo balloon will be 30 mm wide.

An aspect of an embodiment of the present invention the presence of two balloons placed in the last quarter of the whole length of the probe, and inflating toward opposite positions, a cryo balloon or also referred to as a ablation balloon, is included in a larger protective balloon that fully surrounds and incorporate the other one leaving only an "operating window". The former is inflated with a cryogen gas (i.e, liquid nitrogen, nitrous oxide, carbon dioxide or Argon) whereas the latter will be filled with a thermal medium or other solution, having a high thermal conductivity. The epicardial balloon with heat sink-like solution inside will protect the surrounding anatomic structures (oesophagus, lungs, coronary arteries, and phrenic and vagus nerves by keeping them close to their physiological temperature).

This overcomes one of the main limitation of known catheters and with the proposed catheter unit a novel way of protecting the surrounding structures is introduced.

When the cryoprobe is in place and safely fully surrounded by the protective balloon, the temperature in lowered, e.g. to −20 degrees, that will allow the complete alignment and coupling of the endocardial catheter with the endocardial one. Only at this stage the system is ready for cryoablation and the temperature can be lowered down to −80 degrees, depending on what is desired.

Compared to known ablation catheters that provide energy in all directions the catheter according to the present disclosure is able to focus its energy and thus the ability to direct at least a great part of the energy in one direction, and will ablate only the chosen target, sparing the other regions of the heart. The ablation catheter is kept firmly in place on both surfaces and kept in place by the glue-like effects of extremely low temperatures and the surrounding protective balloon will leave only a “working window” that will correspond to the target lesion and the only place where the energy is delivered.

Furthermore, known the ablation tools used in the endocardial or epicardial surface, has been proved not to guarantee the full transmurality. With the proposed endo-epicardial system approach and perfect coupling of the catheters all the depth of the heart wall is reach by a sufficient energy to lead to cellular death. The deepest central part of the wall is targeted from both sides that guarantees its reliable and safe ablation.

The proposed epicardial catheter is placed against the target heart tissue and the rest of the catheter is surrounded by the cooling catheter. This guarantees the perfect contact between the catheter and the heart tissue, without blood interposed It has been found that irrigated catheters make deeper, larger lesions than non-irrigated-tip catheters. The limitations of irrigation technique is that, filling the small pericardial space with just 100 cc (corresponding to just under 6 minutes of ablation if the infusion rate is 17 cc/min) causes hemodynamic stability. For this reason the fluid release in the pericardium must be sucked back by an efficient suction system able to suck the same amount of irrigation fluid provided/per minute.

The present disclosure solves the problem posed by the use of irrigated tips by use of a separate suction channel that allows for removal of the irrigation fluid from the pericardium at a rate sufficient to overcome the problems related to the infusion of the liquid. Another advantage of suction associated with an aspect of an embodiment of the present invention would arise if there was a perforation of the heart, which may occurs in a not negligible number of cases.

The protective epicardial balloon shows plenty of holes on its surface through which the cooling liquid goes outside in the pericardial sac and it is drained by some small holes over the tip of the catheter connected to the inner suction lumen. The endocardial balloon does not have this mechanism. Indeed, the cooling liquid cannot go inside the heart chambers since the overload could lead to cardiac failure. The cooling liquid flows inside the balloon within a closed circuit at a desired velocity and it is aspired back to a reservoir when its temperature rises beyond an established value. Such a closed-circuit design could be applied also to the epicardial catheter.

The epicardial balloon is designed to obtain a balance between irrigation volume and turgidity: depending on the millilitres per minute of the liquid delivered and the diameters of the holes on its surface, it ensures contemporary adequate cooling and protects physically neighboured organs from useless and potentially unsafe involvement of healthy tissues.

Thus, when placing the catheter against the target area, the tip of the catheter may damage adjacent structures. Most of the catheters have long tips that must be handled with great caution to avoid complications.

The tip, in an example of the proposed catheter, when the two balloons are completely inflated, is fully embedded and it will not be in contact with the tissue. The tip margins are smooth. The tip is in an example, able to open to allow the passages of other catheters (e.g. mapping, pacing etc).

A cross-sectional view of the catheter unit may in an example show a multi-lumen configuration to accomplish all the features of the device. It comprises a separate line for the delivery of the liquid to the protective balloon, and another one for the cryogen gas supply to its correspondent balloon. There is also an outflow lumen for the suction liquid coming from the suction holes on the body of the catheter. In this section are visible the four steering tendon to bend the catheter. The middle lumen is thought to be used for a pre-curved shaft to ease the placement of other catheters over different anatomical areas of the heart for different purposes (mapping).

The unit may in an example also comprise one or more electrodes, surrounding the catheter shape and placed between the length of the balloon for the cryogen ablation for the evaluation of electrical pre and post-treatment activity. Likewise, in an example, a magnetic element is present for a possible magnetic guidance development, and thus a remote magnetic placement of the device. In another example, radiopaque markers are present at different levels on the catheter for a radioscope visualization.

The endocardial catheter is in an example composed of the catheter main body put into a common or specifically designed transeptal sheath—in case of AF ablation. The introducer is designed for being introduced into a peripheral vessel and, once in place, crossing the interatrial septum through the needle, being retracted, leaving the main body free to move inside the left atrium.

The shape of the endocardial element is preferably the same as the epicardial one. The endocardial catheter is not less than 100 cm with the cryo balloon 30 mm wide. The endocardial unit comprises a cryo and a protection balloon embedding the former and leaving a “working window” space where the cryo energy can be fully delivered. The tip is fully embedded into the inflated balloons. This system is isolating the catheter from the moving blood improving the performance of the catheter and, at the same time, avoiding freezing blood damage.

Nonetheless, to avoid, dilution and fluid overload of the patient, when the catheter is not irrigated, the protecting endocardial balloon in an example does not have holes, as well as there are not suction holes on the body of the endocardial balloon. The protective balloon may be inflated with a continuous flow to keep the temperature of the balloon constant and, consequently that of the blood. The section of the endocardial balloon will show an inlet and outlet port, which are in communication each other, creating a close circuit.

Different sizes of the balloons will fit different size of patients’ heart chambers. However, small adjustment will be allowed by a differential insufflation of the cryo balloon. In an example, a biocompatible material is employed in the housing of the system.

The system may be provided, in an example, with an ergonomic handle, configured at the proximal end of the unit, which will allow the steering of the catheter. It can be steered by ganging the length of the tendons embedded in the wall of the unit. By changing the relative length of the tendons the bending direction and amount of steering can be modified by rotating a ring with an internal sprocket located at the base of the handling.

The system is designed for the following functional steps: for AF ablation application using the subxiphoid route, once performed a percutaneous subxiphoid access the epicardial catheter is driven through the pericardium sac without opening the pleura. Once inside the pericardium sac, the catheter is placed in the area of interest. Simultaneously, the endocardial catheter is introduced into a peripheral vessel, pushed into the right atrium and the interatrial septum, and placed in the same area of the epicardial element. After checking their positioning through radioscopy, the cryo balloons are gradually inflating with a mild low temperature to fix the elements to the tissue. After checking again the correct alignment, the temperature is dropped down to the therapeutic level until obtaining a reliable lesion. The epicardial catheter cooling system is activated simultaneously with the temperature drop, protecting the oesophagus and other neighboured tissue from being ablated.

With the proposed catheter unit, one of the biggest drawbacks of the cryogenic energy used in cardiac ablation is overcome, being the scarce penetration of the lesion, letting residual portion of the ablated atrial responsible for electric reconnection. Indeed, the biparietal placement of the energy sources may produce a deeper lesion with less energy employed and less length of the whole procedure.

BRIEF DESCRIPTION OF THE DRAWINGS

The ablation catheter system according to the present disclosure will further be explained with reference to the drawings, wherein.

DETAILED DESCRIPTION OF THE DRAWINGS

Figure 1A:
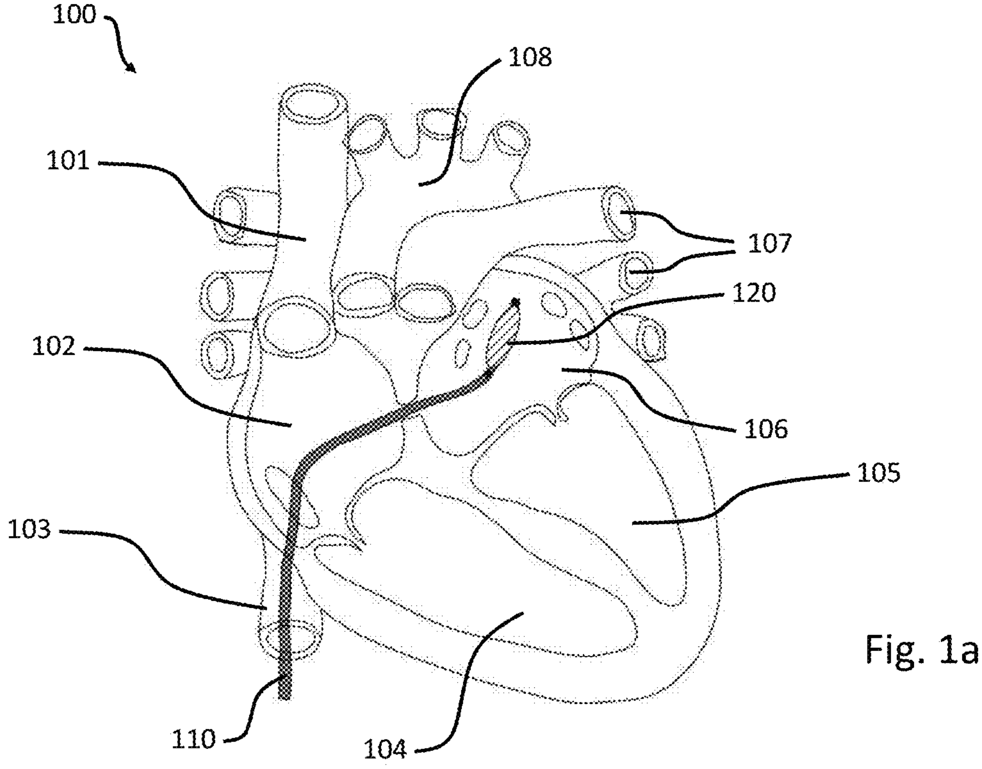
FIGS. 1*a* and 1*b* show a heart and endocardial catheter unit according to the present disclosure, when inserted into the heart and in relation to the oesophagus.

FIG. 1*a* shows a schematic view of a heart with several of the ventricles, veins, atrium and aorta. It can be seen that the catheter unit 110 can be inserted into the heart 100 through the inferior cava vein 103.

The subject shown in FIG. 1*a* is the heart 100 of a human in which the catheter according to the disclosure is used. It is expressed, that this is just an example and that the catheter system may also be used for performing ablation treatments on other parts of the human body or even more in general on any tissue of a subject being a mammal.

In particular, the catheter is configured to perform ablation which is a process that uses cold, i.e. extreme cold, to destroy the operative tissue. The catheter is the probe to administer the ablation medium which in the present disclosure is a cryo ablation medium and in particular a freezing medium such as nitrogen oxide or carbon dioxide.

Cryo ablation is in particular a highly suitable method of treatment to restore the normal heart rhythm by disabling tissue that creates or adds to irregularities of the heartbeat. Cryo ablation is a limited invasive procedure in which a catheter is inserted into or near the heart to locate the operative tissue which is selected as the target tissue for freezing that tissue such that the irregularities of the heartbeat are prevented.

In cryo ablation, typically, a catheter is inserted into a blood vessel, e.g. a vessel in the upper leg, and then threaded through the body until the catheter tip reaches the heart. In the ablation catheter a balloon is present which can be inflated and once inflated, the cryo medium can be introduced into the balloon to lower the operative tissue adjacent the balloon and thereby killing the target tissue.

There are several challenges in the procedure of such cryo ablation, e.g. being able to guide the endocardial catheter into the heart, performing ablation in such a way that a true biparietal ablation is achieved, and to prevent damaging the tissue surrounding the operative tissue as much as possible for the cold of the cryo medium.

Most known techniques of performing cryo ablation are not able to perform true biparietal ablation, which means that the tissue between the outer wall surface of the heart and the interior of the wall is fully destroyed or in other words, that the depth of the ablation into the tissue of the heart reaches throughout the opposite surface.

The catheter according to the present disclosure is able to perform such true biparietal ablation. To this end, the catheter system comprises two catheter units, an endo and an epi catheter which are designed such that these can align effectively, and perform an effective biparietal ablation without damaging surrounding non-targeted tissue.

FIG. 1*a* the endocardial catheter 110 positioned inside the heart 100, and also shows the superior cava vein 101, the right atrium 102, the inferior cava vein 103, the right ventricle 104, the left ventricle 105, the left atrium 106, the pulmonary veins 107 and the aortic arch 108.

The catheter system according to the present disclosure is thus arranged to perform tissue ablation on such a heart 100, for example for atrium fibrillation but is not limited to such applications only. The system is arranged for creating a transmural or biparietal lesion of operative tissue of a subject, here the heart of a person.

To this end, the catheter units of the catheter system are configured as flexible catheter units, of which one being the flexible epicardial catheter unit and the other the flexible endocardial catheter unit 120, which is shown in FIG. 1*a*.

Figure 1B:
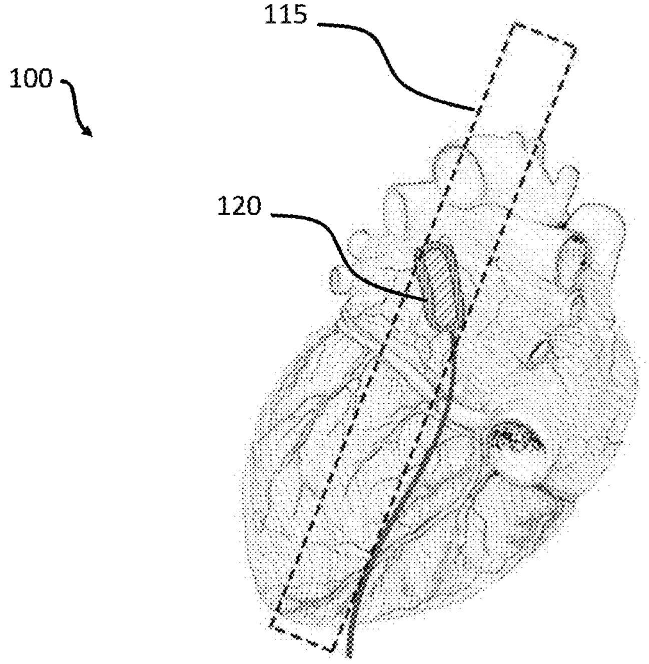

In FIG. 1*b* a posterior view of the heart 100 is shown in relation to the esophagus 115 (dotted line) and the catheter 115 put in place.

Figure 2:
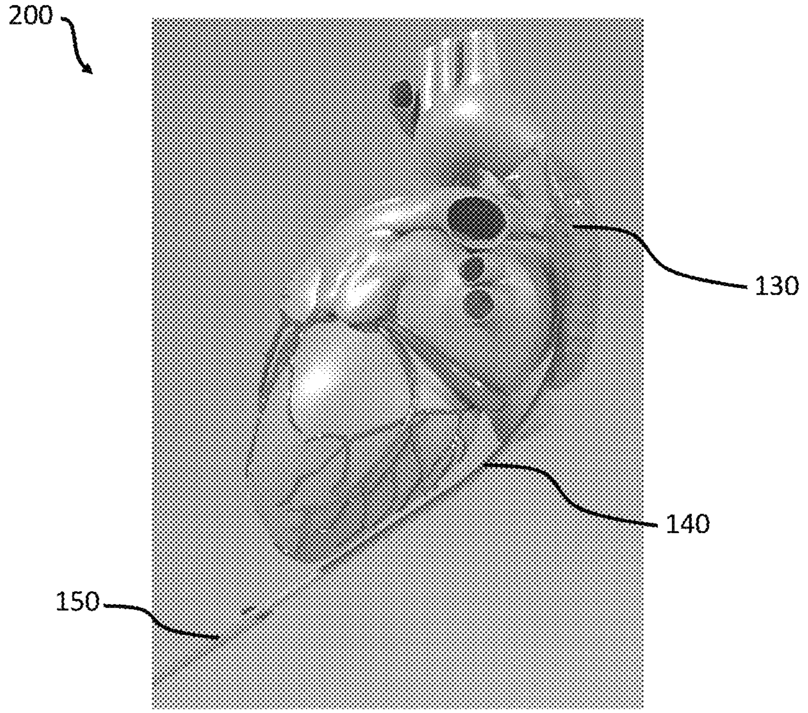
FIG. 2 shows a picture of a heart and an epicardial catheter unit according to the present disclosure, when inserted near the heart.

In FIG. 2 a picture is shown of a heart 200 with a detail of the other catheter unit, i.e. the flexible epicardial catheter unit 200. This catheter unit has a catheter tip 130, a drivable catheter body 140 and a subxiphoid introduction trocar 150.

As can be seen in FIG. 2 the catheter is in use and comprises two balloons, a cryo balloon 131 or also referred to as ablation balloon for administering cold to the tissue which is to be ablated. The ablation may be performed with an ablation medium or cryo ablation medium, or freezing medium, more in particular, a nitrous oxide or carbon oxide or carbon dioxide, which is administered to the inflated balloon and arranged to ablate the posterior wall of the heart. The protective balloon 135 is arranged to protect the neighbouring tissues from the cryo ablation effects, i.e. the cold administered to the targeted tissue which may arrive at non-targeted tissue.

Figure 3:
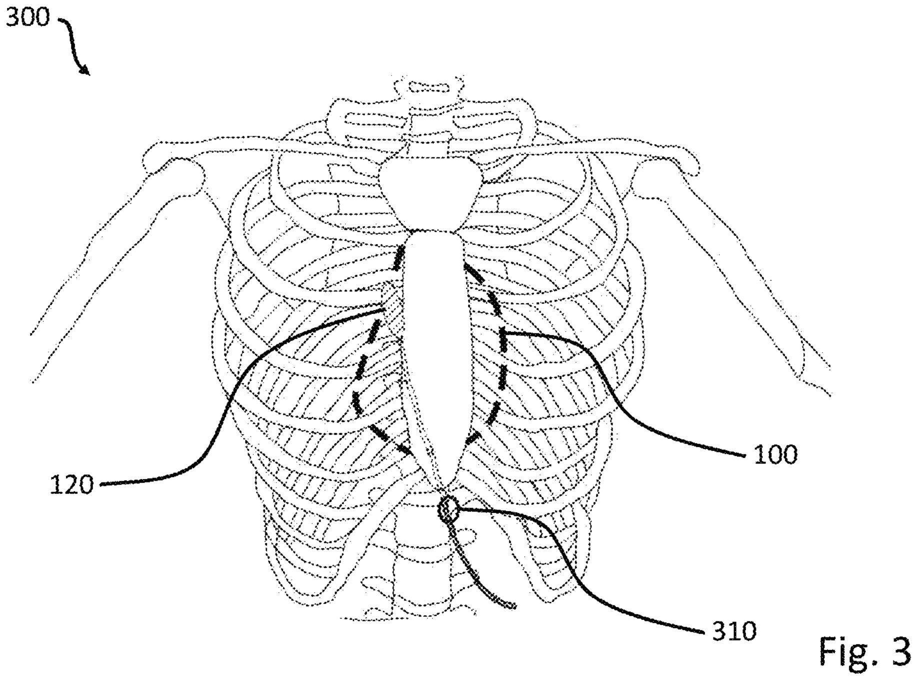
FIG. 3 shows the breast of a person and the location of subxiphoid access of the epicardial catheter unit according to the present disclosure, when inserted into the heart.

In FIG. 3 the chest 300 of the subject is shown, and the way in which the epicardial catheter unit 120, 200 is inserted into the chest 300 and heart of the subject through the subxiphoid access 120.

Figure 4A:
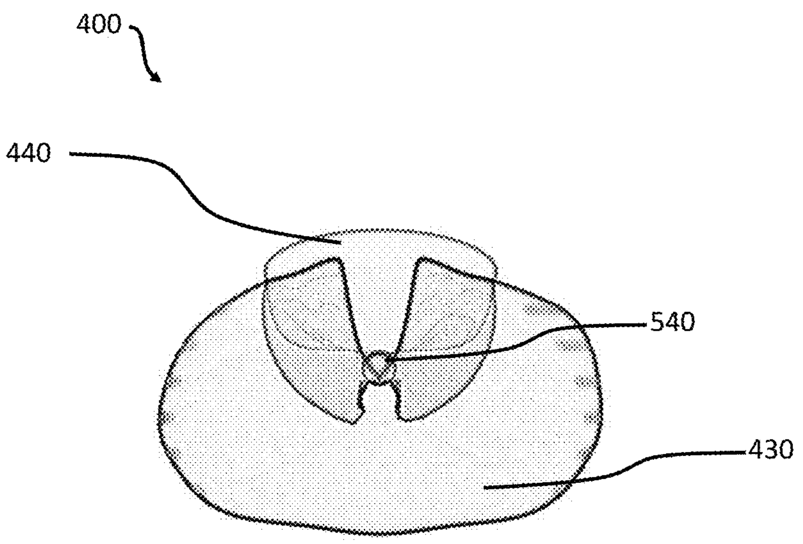
FIGS. 4*a* and 4*b* shows the biparietal placement and biparietal effect of the two catheters according to the present disclosure in different perspectives.

In FIG. 4*a* a frontal view is shown of the catheter 400, showing the protective balloon 430 surrounding the cryo balloon 440 and leaving out only the ablating area.

Figure 4B:
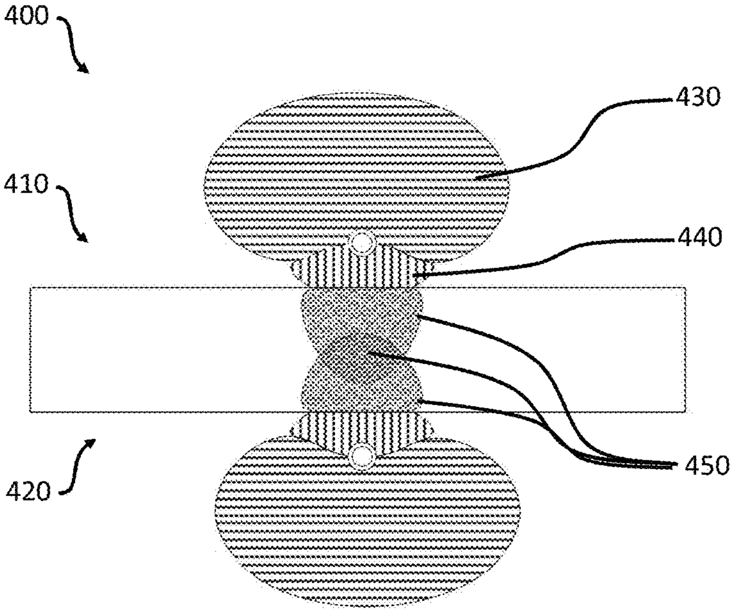

In FIG. 4*b* show the two sides, interior and outer side, of the heart or operative tissue. In particular the top tide or outer side is the epicardium 410, and the bottom side or inner side is the endocardium 420.

As can be seen, the epicardial catheter unit 411 comprises a cryo balloon 440 or ablation balloon to perform the cryo ablation. The epicardial catheter further comprises a protective balloon 430 which surrounds the ablation balloon 440 to prevent tissue damage to non-targeted tissue. On the endocardial side 420, a similar configuration is shown in which the endocardial catheter unit 412 also comprises a ablation balloon or cryo balloon and a protective balloon to surround the cry balloon in the same or similar manner as at the epicardial side 410. Since the ablation is performed from two sides, the ablated area 450 overlaps and thereby a true biparietal ablation can be achieved.

Figure 5:
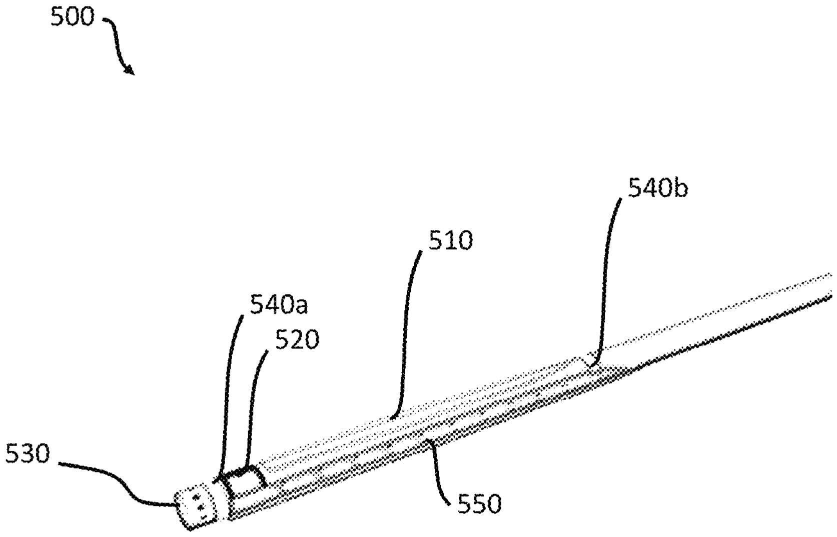
FIG. 5 shows one of the catheter units according to the present disclosure.

In FIG. 5 a catheter unit 500, e.g. epicardial or endocardial or both, is shown. The catheter unit comprises several components, being the actual cryo balloon 510 on the top side of the wall surface of the unit 500, on the other side of the wall surface of the unit 500 is the protective balloon 550. Also the catheter comprises a magnet 520 for localization and alignment with the other catheter unit. The magnet is preferably located at or near the tip. The catheter 500 also comprises one or more electrodes 540*a*, 540*b*, for localisation, and at the tip, is comprised of a suction element 530 as intake for the protective medium which may flow out of the protective balloon 550 into the area at which the ablation is performed.

The catheter is preferably manufactured of a flexible material which has a cavity to transport the protective medium, in particular at least the protective medium and preferably also the cryo or freezing medium, away from the operative tissue. The supply of the two mediums, i.e. the cryo medium and the protective medium, may be arranged separately. At the top, one of the passages or channels is arranged as an intake to supply the cryo medium such as the nitrogen gas, whereas at the bottom, a passage or channel is arranged as another intake for the supply of the protective medium such as a water or water based coolant. At four opposing sides, inside the wall surface, the catheter is further provided with steel tendons. These steel tendons operate as steering mechanism by pulling or tensioning one or several of these tendons to steer the catheter into the desired direction.

Figure 6:
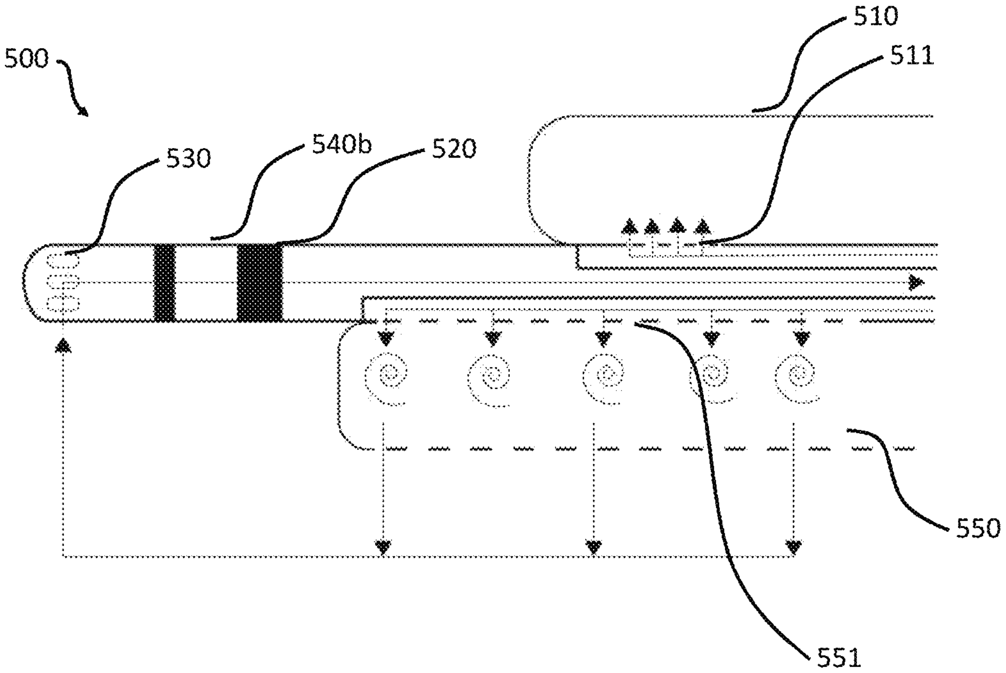
FIG. 6 shows a schematic view of one of the catheter units according to the present disclosure.

FIG. 6 shows, in an illustrative manner, the inside of the catheter 500. At the tip, a magnet 520 is provided and an electrode 540*b*. At the top the cryo balloon or ablation balloon 510 is shown, fully or partly inflated. The balloon allows the cryo medium to enter the balloon 510 through opening or ports 511 in the top of the catheter 500. The balloon at the bottom is the protective balloon 550 and allows the protective medium to enter the balloon 550 through openings or ports 551 in the bottom of the catheter 500.

Figure 7A:
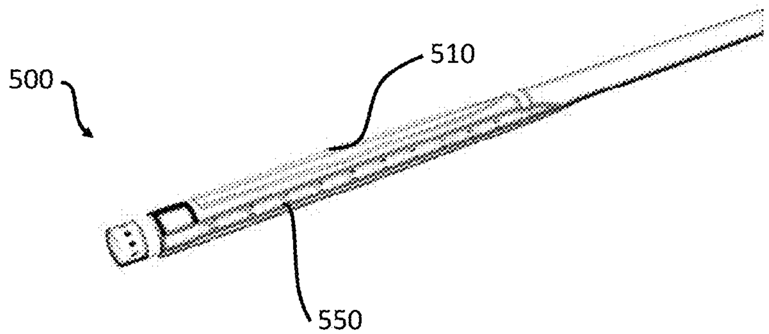
FIG. 7*a-c* show the different stages of use of the catheter units according to the present disclosure.
Figure 7B:
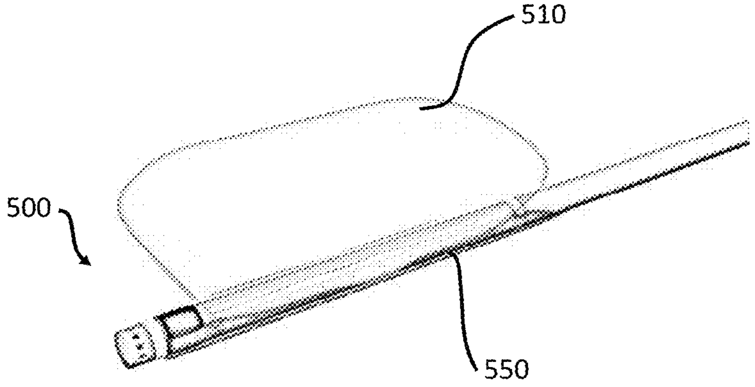
Figure 7C:
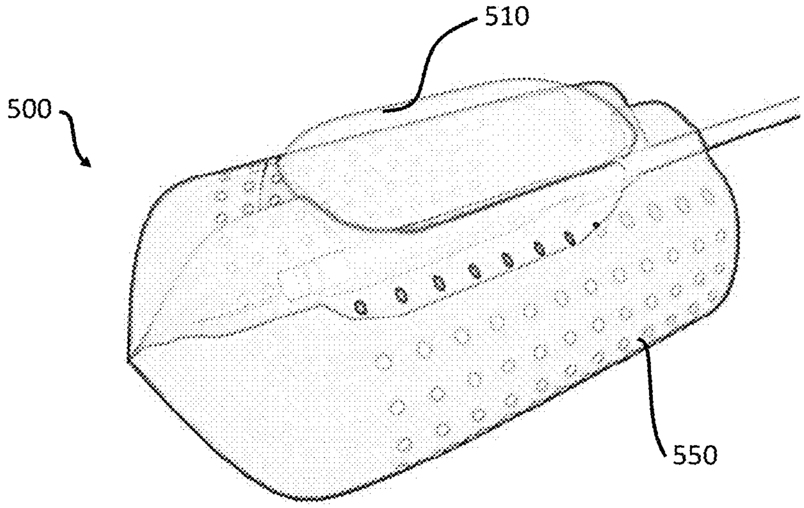

FIG. 7*a-c* shown several stages of the catheter 500 upon inflation. In FIG. 7*a* the catheter is not yet inflated and in a mode of operation which is suitable for steering the catheter tip towards the desired and targeted operative tissue. Once in position, the balloons may be inflated which is shown stepwise in FIGS. 7*b* and 7*c*. In step 7*b* the cryo balloon 510 is inflated partly and in protective balloon 550 is not yet inflated, whereas in FIG. 7*c* both 510, 550 are fully inflated. It is expressed that the sequence shown in FIG. 7*a-c* is merely an example, and that the inflating of the balloons may also be performed in parallel, sequentially in which the cryo balloon is inflated first, or the protective balloon is inflated first.

The person skilled in the art will appreciate that the present invention is by no means limited to the preferred embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the scope should not be construed as limiting the scope of the appending claims.

The invention claimed is:

1. An ablation catheter system for biparietal tissue ablation such as atrial, atrio-ventricular or ventricular arrhythmias arranged for creating a transmural lesion of operative tissue of a subject, said catheter comprising:

a flexible epicardial catheter unit comprising a magnet and an ablation element, wherein said magnet is located at a wall section of said catheter unit for magnetic external driving and eventually coupling of said magnet with a magnet of said endocardial catheter unit, and wherein said ablation element is configured as an elongated ablation element along a longitudinal direction of said flexible epicardial catheter unit;

a flexible endocardial catheter unit comprising a magnet and an ablation element, wherein said magnet is located at a wall section of said catheter unit for magnetic external driving and eventually coupling of said magnet with said magnet of said epicardial catheter unit, and wherein said ablation element is configured as an elongated ablation element along a longitudinal direction of said flexible endocardial catheter unit;

said elongated ablation element of both said epicardial and said endocardial catheter unit comprising:

an ablation balloon, and a protective balloon, wherein said ablation balloon is arranged for cryoablation of said operative tissue with a freezing medium flowing through a first exhaust port in a wall section of said catheter into said ablation balloon for subjecting said operative tissue with cold of said freezing medium, and wherein said protective balloon is arranged for protecting (i) tissue alone, (ii) anatomic structures surrounding said operative tissue alone, or (iii) both tissue and anatomical structures with a thermal medium flowing through a second exhaust port in a wall section of said catheter into said protective balloon, and wherein said ablation balloon and said protective balloon are configured for, in use, said ablation balloon to be surrounded by said protective balloon, for protecting said surrounding tissue and/or anatomic structures by removing thermal energy of said freezing medium affecting said surrounding tissue and/or anatomic structures.

2. The ablation catheter system according to claim 1, wherein at least one or both of said epicardial and said endocardial catheter unit further comprises, a steerable catheter body.

3. The ablation catheter system according to claim 2, wherein said steerable catheter body comprises longitudinal tension elements.

4. The ablation catheter system according to claim 3, wherein said longitudinal tension elements comprise a plurality of parallel steel tendons, disposed longitudinal in a wall section of said catheter body.

5. The ablation catheter system according to claim 1, wherein at least one or both of said epicardial and said endocardial catheter units comprise parallel longitudinal channels, connecting said first and second exhaust ports for transport of said freezing medium and said thermal medium, respectively.

6. The ablation catheter system according to claim 5, wherein at least one or both of said epicardial and said endocardial catheter units comprise at least one parallel longitudinal channel connecting said first exhaust ports for transport of said freezing medium to said ablation balloon, and at least one parallel longitudinal channel connecting said second exhaust ports for transport of said thermal medium to said protective balloon, respectively, and at least one parallel longitudinal channel connecting an exhaust ports for removing said freezing medium and said thermal medium away from said ablation balloon and said thermal balloon.

7. The ablation catheter system according to claim 1, wherein at least one or both of said epicardial and said endocardial catheter units comprise one or more electrodes.

8. The ablation catheter system according to claim 1, wherein said freezing medium comprises one or more of the group of: nitrogen oxide, carbon dioxide, cooling or freezing liquid, cooling gas.

9. The ablation catheter system according to claim 1, wherein said system further comprises a subxiphoid introduction trocar.

10. The ablation catheter system according to claim 1, wherein said magnet of at least one or both of said epicardial and said endocardial catheter units comprise a magnet in a wall section corresponding to a section housing said ablation balloon, directing towards the operative tissue, for epicardial catheter unit and said endocardial catheter unit to be guided and placed over targeted areas by said magnets of said epicardial catheter unit and said endocardial catheter unit to attract, and wherein in particular, the magnetism attraction may be used for the ultimate alignment of said epicardial catheter unit and said endocardial catheter unit.

11. The ablation catheter system according to claim 1, wherein said protective balloon of at least one or both of said epicardial and said endocardial catheter units having larger dimensions than said ablation balloon.

12. The ablation catheter system according to claim 1, wherein said first exhaust port of at least one or both of said epicardial and said endocardial catheter units comprise a pattern of first exhaust subports, disposed in a one or preferably two-dimensional array of subports.

13. The ablation catheter system according to claim 1, wherein said second exhaust port of at least one or both of said epicardial and said endocardial catheter units comprise a pattern of first exhaust subports, disposed in a one or preferably two-dimensional array of subports.

14. The ablation catheter system according to claim 12, wherein said subports are disposed in a two-dimensional array, disposed at regular intervals along a longitudinal direction of said catheter.

15. An ablation catheter system for tissue ablation such as atrial fibrillation, arranged for creating a transmural lesion of operative tissue of a subject, said catheter comprising:

an epicardial catheter unit comprising a magnet and an ablation element, wherein said magnet is located at a wall section of said catheter unit for magnetic external driving and eventually coupling of said magnet with a magnet of said endocardial catheter unit, and wherein said ablation element is configured as an elongated ablation element along a longitudinal direction of said flexible epicardial catheter unit;

an endocardial catheter unit comprising a magnet and an ablation element, wherein said magnet is located at a wall section of said catheter unit for magnetic external driving and eventually coupling of said magnet with said magnet of said epicardial catheter unit, and wherein said ablation element is configured as an elongated ablation element along a longitudinal direction of said flexible endocardial catheter unit;

a medium supply arrangement, arranged for providing freezing medium and thermal medium to an ablation element, a group of ablation elements, or all ablation elements, of said epicardial and endocardial catheter unit either consecutively or simultaneously; and a control unit arranged for controlling steering of at least one or both of said epicardial and said endocardial catheter units and for controlling inflating, deflating and flow of freezing medium and thermal medium to said epicardial and endocardial catheter unit.

* * * * *